United States Patent [19]

Eisenlauer et al.

[11] Patent Number: 4,752,131

[45] Date of Patent: Jun. 21, 1988

[54] LASER-OPTICAL ARRANGEMENT FOR MEASURING THE DEGREE OF DISPERSION IN FLOWING SYSTEMS

[75] Inventors: Josef Eisenlauer, Ludwigshafen; Dieter Horn; Walter Ditter, both of Heidelberg; Heinz Eipel, Bensheim, all of Fed. Rep. of Germany

[73] Assignee: BASF Aktiengesellschaft, Ludwigshafen, Fed. Rep. of Germany

[21] Appl. No.: 717,107

[22] Filed: Mar. 28, 1985

[30] Foreign Application Priority Data

Apr. 4, 1984 [DE] Fed. Rep. of Germany ....... 3412620

[51] Int. Cl.$^4$ ........................................... G01N 21/53
[52] U.S. Cl. ................................... 356/338; 250/564; 250/573; 356/442
[58] Field of Search ............... 356/336, 338, 441, 442; 250/564, 573

[56] References Cited

U.S. PATENT DOCUMENTS

| | | | |
|---|---|---|---|
| 3,899,688 | 8/1975 | Perieres | 356/442 X |
| 4,072,421 | 2/1978 | Coyne et al. | 356/442 X |
| 4,110,044 | 8/1978 | Pettersson et al. | 250/524 X |

OTHER PUBLICATIONS

McFadyen et al., "An Automatic Flow Ultramicroscope for Submicron Particle Counting and Size Analysis", *J. Of Colloid and Interface Science*, vol. 45, No. 3, pp. 573–583, 12/73.
Colloid and Polymer Sci. 258 (1980) S.1303.
Colloid and Interface Sci. 17 (1962), S.605.

*Primary Examiner*—Davis L. Willis
*Assistant Examiner*—Matthew W. Koren
*Attorney, Agent, or Firm*—Keil & Weinkauf

[57] ABSTRACT

In a laser-optical arrangement for producing signals by light scattering, obscuration or reflection, from flowing particles and/or groups of particles, which are recorded, as time-dependent voltage/current fluctuations, by means of a photodetector (9) via appropriate imaging optics (7,8,18), assignment to the degree of dispersion of the flowing system is based on a subsequent measurement (10) of the root-mean-square value, and, according to the invention, the sample stream (1) is separated from a transmitter (6,7,18) and a receiver (8,9,10) by an enveloping stream (4), and the transmitter side consists of an individual light-transmitting fiber (7) provided with a means for parallel or focused emergence of a light bundle having a diameter of the order of magnitude of the particles and/or groups of particles.

6 Claims, 3 Drawing Sheets

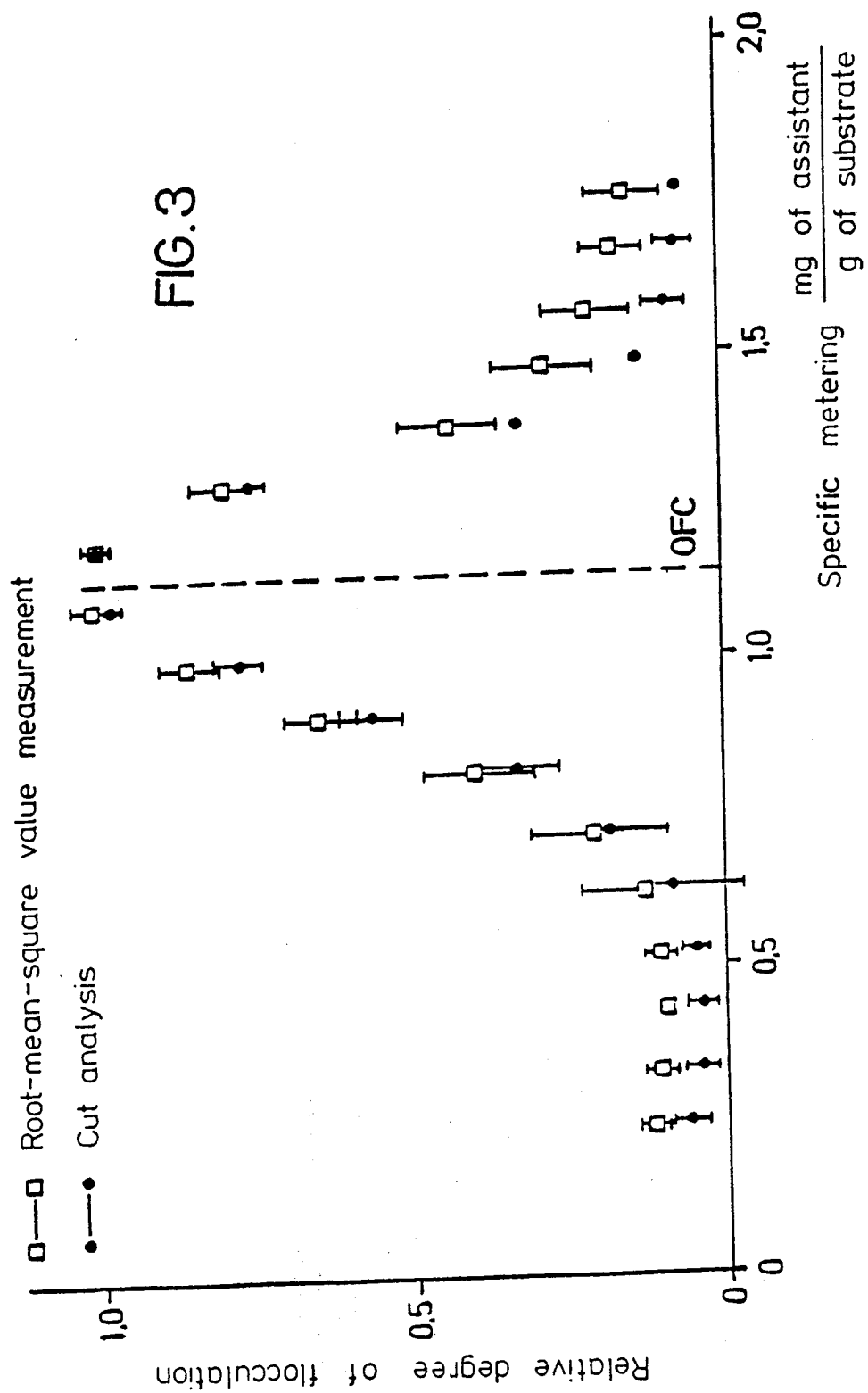

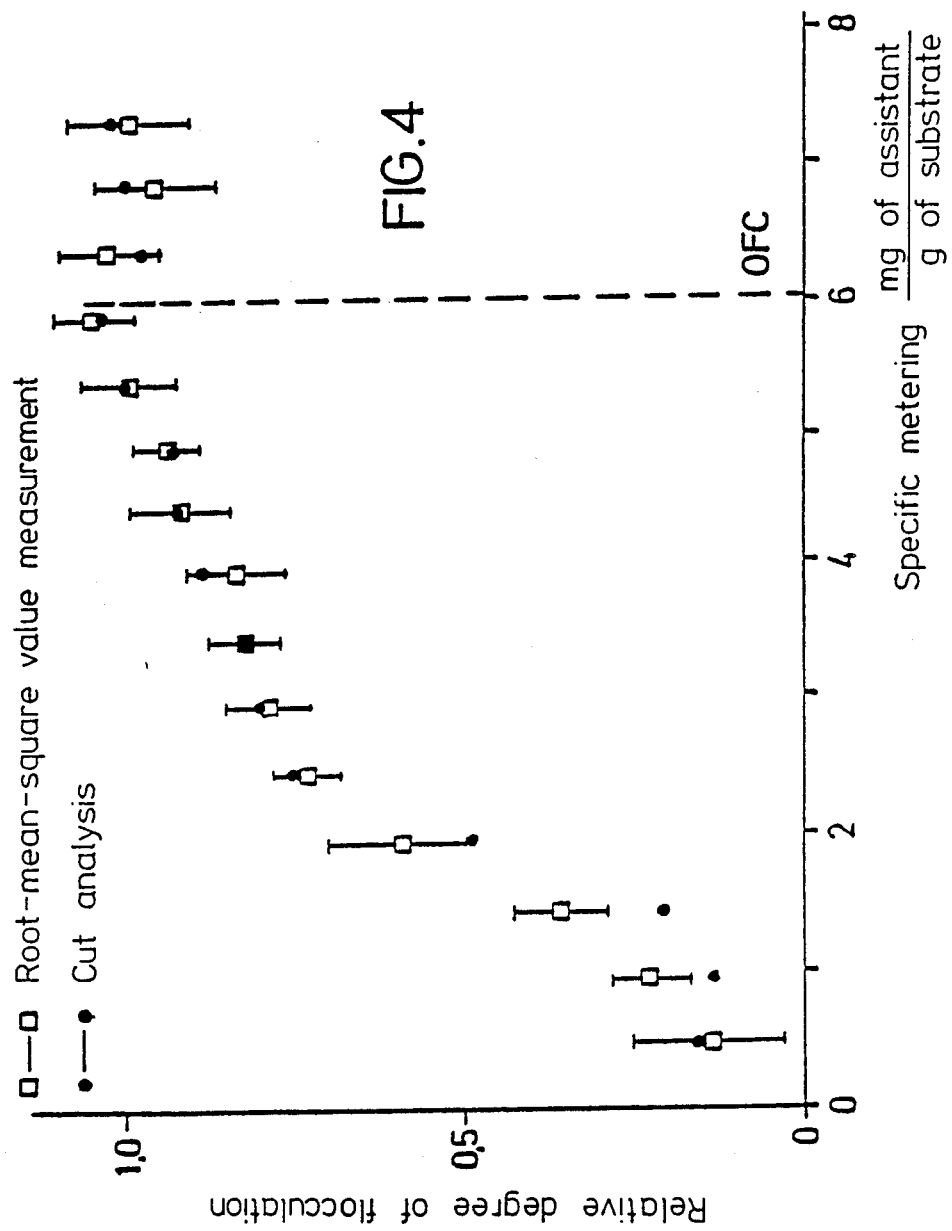

LASER-OPTICAL ARRANGEMENT FOR MEASURING THE DEGREE OF DISPERSION IN FLOWING SYSTEMS

The present invention relates to a laser-optical arrangement for the rapid in situ measurement of the degree of dispersion in flowing two-phase systems, in particular for the determination of the optimum metering of dispersants or flocculants in relatively highly concentrated dispersions satisfying the requirements of practice.

A rapid in situ measurement of the degree of dispersion in a flowing system can be used for two different purposes. On the one hand, it is possible to monitor the course of dispersion in industrial comminuting apparatuses. In this case, the effect of apparatus parameters and dispersants can be investigated. One example of this is wetcomminuting with the addition of dispersants. On the other hand, the laser-optical method is employed for the measurement of the selective destabilization of systems as a result of the addition of flocculants. The laseroptical method makes it possible to carry out both measurements in situ, so that very rapid changes in the degree of dispersion as a result of selectively metering in assistants can be detected. Moreover, the degree of dispersion can be measured under the specific shear stress of the flowing system.

As a result of these properties, the laser-optical method appears suitable both for use in laboratory tests for assessing the mode of action of dispersants or flocculants and for the on-line monitoring and regulation or control of dispersing or flocculating plants.

The laser-optical method is based on the measurement and evaluation of signals from flowing particles and/or groups of particles, which signals are produced by light-scattering, obscuration or reflection and fluctuate with time. One possible technical realization in the form of scattered-light counters is known, and is described in the literature (Colloid & Polymer Sci. 258 (1980), 1303).

In this method, the apparatus is designed so that the measurement, which is effected in a flow-through cell, is carried out not on a particle ensemble, as in the case of a simple turbidity measurement, but on individual particles. This can be done either by focusing the laser light to a beam diameter of the order of magnitude of the particles to be measured (Colloid & Polymer Sci. 258 (1980), 1303) or by isolating the particles in capillary flow (Colloid & Interface Sci. 17 (1962), 605). The latter method has the disadvantage that extreme shear stresses can occur during flow through the capillaries and, owing to the limited resistance of groups of particles to shear forces, these stresses may lead to a nonrepresentative degree of dispersion. Moreover, use in systems in practice (sewage sludge, waste water, etc.) is prevented by the high susceptibility to problems as a result of blockages.

The pulse-like detector signals recorded by a photodetector are assigned to a particle size distribution as a rule by means of multi-channel analyzers, which carry out a pulse count and classification of pulse heights (pulse height analysis). However, pulse height analysis is restricted to relatively dilute systems, where the signal to be measured consists of isolated individual pulses without overlap. Owing to the relatively high concentration and the presence of groups of particles, practical systems generally give overlapping and structured pulse sequences on a high DC background; this cannot be evaluated using the principle of pulse height analysis. For such systems, a modified analytical method (cut analysis) has been proposed in the literature; this method permits very sensitive detection of the optimum metering of flocculants or dispersants into dispersions satisfying requirements of practice, and also gives information on the structure and size of groups of particles (The Effect of Polymers on Dispersion Properties, pages 324–342, Academic Press, London 1982). These differential measurements on individual particles respond substantially more sensitively to changes in the degree of dispersion than does an integral turbidity measurement as described in the literature for the regulation of flocculation plants (GWF-Wasser/Abwasser 121, 6 (1980), 277 and 123,3 (1982), 131).

The analysis can be substantially simplified by means of a simple determination of the root-mean-square value of the pulse-like detector signals (Wochenblatt für Papierfabrikation 13 (1972), 494, and Advances in Solid-Liquid Separation, pages 172–182, Gregory J. (Ed.), Academic Press, London 1984). The close correlation between the root-mean-square value and the degree of dispersion at least permits sensitive detection of the optimum metering of dispersants/flocculants; moreover, information about the size and structure of the particles and/or groups of particles is also provided.

The previous technical versions of optical methods for measuring the degree of dispersion in flowing systems are restricted to dilute systems and carried out using expensive optical and electronic apparatus, as in the case of the measurements on individual particles. Versions which are relevant in practice, suitable for fairly highly concentrated systems and employ comparatively simple electronics for evaluation can be realized only by the use of complicated optical assemblies and/or of thin capillaries as flow-through cells, with a corresponding danger of blockage. In all versions, deposits on the windows of the flow-through cells have particularly disadvantageous effects. This applies particularly to the use of polymeric flocculants (for example for wastewater treatment or sludge dewatering), where tacky flocs can block the flowthrough cells mechanically and/or optically in a very short time. The turbidity measurement is known to be particularly susceptible to problems in this respect, and, because of the substantially poorer resolution compared with the differential methods, cannot in any case be considered as a reliable method in practice.

It is an object of the present invention substantially to simplify the hydraulic and optical design and data analysis for the differential optical assessment of the degree of dispersion in flowing systems, and to adapt the said design and data analysis to the special circumstances in fairly highly concentrated systems satisfying practical requirements, in order in this way to extend the range of possible uses beyond the laboratory sector and into practical applications.

We have found that this object is achieved by a laser-optical arrangement for producing signals, photoelectrically from flowing particles and/or groups of particles, which are recorded, as time-dependent voltage/current fluctuations, by means of a photodetector via imaging optics, assignment to the degree of dispersion of the flowing system being based on a subsequent measurement of the root-mean-square value, wherein, according to the invention, the sample stream is separated from a transmitter and a receiver by an enveloping stream, and the transmitter side consists of an individual light-transmitting fiber provided with a means for unidirectional emergence of a light bundle having a diameter of the order of magnitude of the particles and/or groups of particles.

The design of the laser-optical method for measuring the degree of dispersion in flowing systems is further improved, in accordance with the invention, if the photodetector is operated in a clamping circuit which provides a D.C. voltage/current reference value on the basis of which the fluctuations are standardized, if the laser used is an integrated semiconductor laser and the laser light is passed directly via a light guide into the flow-through cell, if the photodetector used is an integrated detector, eg. a silicon avalanche photodiode, and the signals are passed from the point of measurement directly via a light guide to the photodetector, and if the optical and electronic arrangements are fully integrated to form a single measuring system.

The invention is based on a combination of three specific elements which are known per se, ie. the envelopestream cell, the light-transmitting fiber and the root-mean-square measurement of pulsed signals. However, simply combining these three elements does not produce the desired end effect. Only the use of special light-transmitting fibers which provide light bundles which emerge parallel or focused and have dimensions of the order of magnitude of the particles and/or groups of particles, in combination with the envelope-stream arrangement and the assignment of the root-mean-square value to the degree of dispersion, substantially overcomes the disadvantages of the conventional measuring arrangements, these disadvantages having been described above.

The particular advantage achieved with the invention is that a sturdy, simple and economical arrangement with increased resolution and reliability in practical operation is provided. Specifically, complicated optical assemblies and adjustment work are dispensed with, and the method is not restricted to thin capillaries with the associated susceptibility to problems as a result of blockage. Moreover, the envelope-stream arrangement ensures high operational reliability in the form of high accuracy of measurement and a long service life. While retaining the same information content, the expensive electronics of pulse height analysis or cut analysis is reduced to a simple apparatus for measurement of the root-mean-square value, or even to a microchip.

As a result, the degree of dispersion in systems satisfying practical requirements can be measured within $\leq 5$ seconds to give a significant result, without prior dilution being necessary, and, if required, the result can be used as a parameter for regulating or controlling dispersing or flocculation plants. Many novel fields of use in research and industry have been opened up for the first time.

Four examples of the invention are illustrated below and described in detail.

FIG. 3 shows the relative degree of flocculation of an anionic latex dispersion as a function of the concentration of a cationic flocculant, determined from cut analysis (.—.) and from measurement of the root-mean-square value ($\square$) of the detector fluctuations, using the arrangement shown in FIG. 1.

FIG. 4 shows the relative degree of flocculation of a clay suspension as a function of the concentration of a cationic flocculant determined from cut analysis (.—.) and from measurement of the root-mean-square value ($\square$) of the detector fluctuations, using the arrangement shown in FIG. 1.

Figure 1:
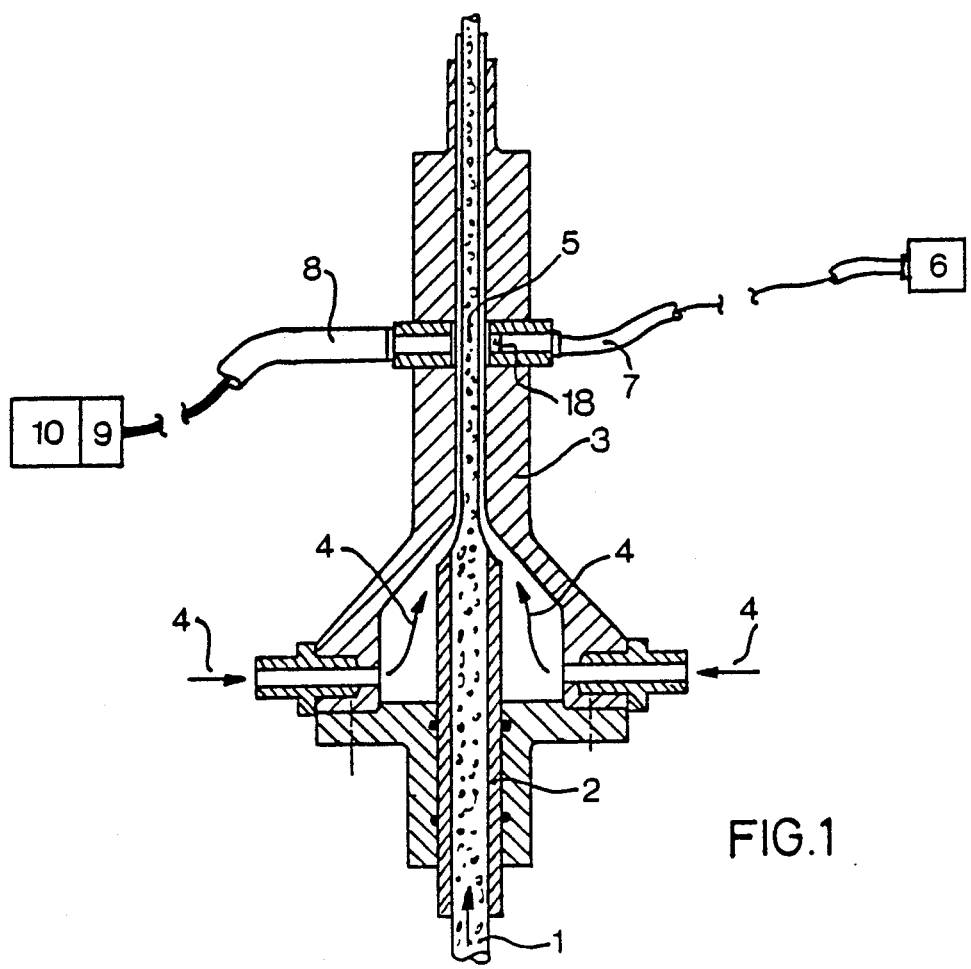
FIG. 1 shows a typical embodiment of a completely integrated laser-optical arrangement for assessing the degree of dispersion in flowing systems.

The dispersion 1 is passed via an axially adjustable inlet nozzle 2 into an envelope-stream cell 3, is surrounded by an enveloping stream 4 and is fed past a measuring point 5. The transmitter side consists of a semiconductor laser 6, and an individual light-transmitting fiber 7 with a lens arrangement 18 for parallel emergence of the laser light so that the light bundle has a diameter of 50 $\mu$m; on the receiver side, the pulselike fluctuations of the light passing through are passed via a light-transmitting fiber bundle 8 to a detector 9 with a means 10 for integrated measurement of the root-mean-square value.

Figure 2:
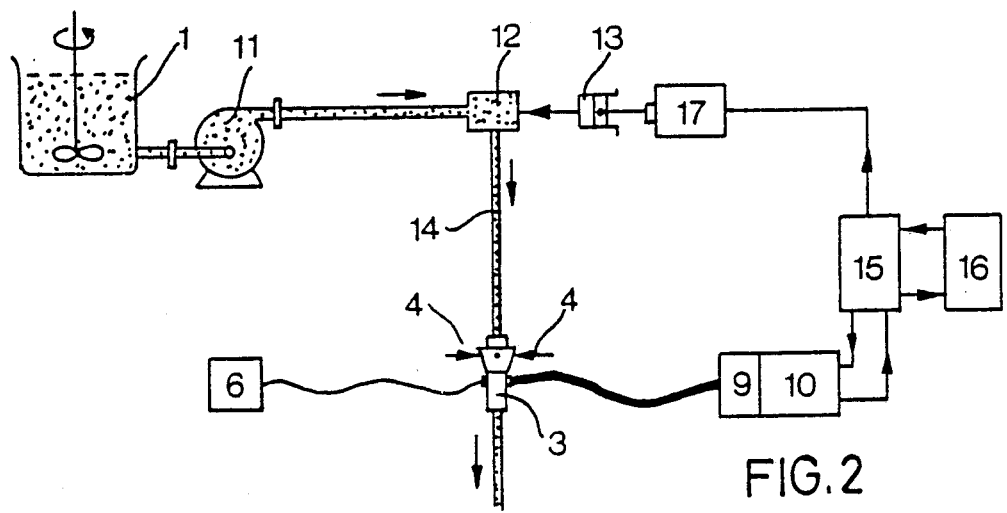
FIG. 2 shows the laser-optical arrangement according to FIG. 1 integrated in a computer-controlled unit for testing the efficiency of dispersants/flocculants.

In FIG. 2, the laser-optical arrangement 1–10 is integrated in a computer-controlled unit for testing flocculants.

The dispersion 1 to be flocculated is mixed with the flocculant 13 via a pump 11 in a mixing element 12; when an appropriate amount is metered in, the dispersion is destabilized. The formation of flocs takes place during flow in a pipe. After a variable length of flow 14, the degree of dispersion is determined in a flowthrough cell 3 by means of the novel laser-optical arrangement shown in FIG. 1.

Metering 13 of the assistant and measurement 10 of the root-mean-square value are coupled via a system control 15 in combination with a minicomputer 16. In order to determine the optimum metering of the assistant, the metering 13, 17 can be increased stepwise while the degree of dispersion is determined simultaneously, using the novel arrangement shown in FIG. 1. The results obtained in this case are typically those shown in FIGS. 3 and 4 in normalized form (relative degree of flocculation (identical to one minus relative degree of dispersion) plotted against the specific metering of assistant, in mg of assistant per g of substrate), together with the corresponding error bars. The maximum value of the degree of flocculation was used in each case for the normalization. For comparison, the degree of dispersion was also determined using the cut analysis method described in the literature (in The Effect of Polymers on Dispersion Properties, pages 324–342, Academic Press, London 1982), and the results are plotted in the form of the relative degree of flocculation, together with the determination according to the invention, in FIGS. 3 and 4.

The comparison shows that, at least with regard to the determination of the optimum metering in the form of the plotted OFC values (optimum flocculation concentration), the two methods of determination give the same information. The novel laser-optical arrangement shown in FIG. 1 can also be used, in combination with the system control 15,16 shown in FIG. 2, and after appropriate programming, for monitoring and controlling dispersing and flocculation plants.

We claim:

1. A laser-optical arrangment for measuring the degree of dispersion in a flowing two-phase system containing flowing particles or groups of particles, said arrangement comprising means for producing pulse-like optical signals from said flowing particles or groups of particles, said producing means including optical transmitting means and optical receiving means, and a measuring cell containing enveloping means for separating said flowing system from said transmitting and receiving means, said transmitting means containing a source of laser light, a first light guide in the form of an individual light transmitting fiber and a lens system for causing a parallel or focused light bundle to emerge therefrom which has a diameter of the order of magnitude of the particles or groups of particles, and said receiving means containing a second light guide in the form of a light-transmitting fiber bundle, and a photodetector for producing from said optical signals time-dependent current/voltage fluctuations, and means for deriving from said fluctuations an integrated measurement of the root-mean-square value, thereby to determine the degree of dispersion.

2. A laser-optical arrangement as claimed in claim 1, wherein the photodetector is operated in a clamping circuit whose D.C. voltage/current value is used as the reference value for normalizing the voltage/current fluctuation.

3. A laser-optical arrangement as claimed in claim 1, wherein the laser is an integrated semiconductor laser, and the laser light is passed directly via said first light guide to said measuring cell.

4. A laser-optical arrangement as claimed in claim 1, wherein said photodetector is an integrated detector, and the signals are passed from the measuring cell directly via said second light guide to the detector.

5. A laser-optical arrangement as claimed in claim 1, wherein the optical and electronic systems of said arrangement are fully integrated.

6. A laser-optical arrangement as claimed in claim 4, wherein the photodetector used is a silicon avalanche photodiode and the signals are passed from the measuring cell directly via said second light guide to the detector.

* * * * *